United States Patent [19]
Blanchard et al.

[11] Patent Number: 5,334,743
[45] Date of Patent: Aug. 2, 1994

[54] CATALYTIC AMMOXIDATION OF SATURATED HYDROCARBONS

[75] Inventors: Gilbert Blanchard, Le Plessis Belleville; Elisabeth Bordes, Vemars; Gilbert Ferre, Livry Gargan, all of France

[73] Assignee: Rhone-Poulenc Chimie, Courvevoie Cedex, France

[21] Appl. No.: 991,170

[22] Filed: Dec. 16, 1992

[30] Foreign Application Priority Data

Dec. 16, 1991 [FR] France .................. 91 15843

[51] Int. Cl.⁵ .......................................... C07C 253/24
[52] U.S. Cl. .................................................. 558/319
[58] Field of Search ...................................... 558/319

[56] References Cited

U.S. PATENT DOCUMENTS

| | | |
|---|---|---|
| 3,365,482 | 1/1968 | Khooblar ............... 558/319 |
| 3,395,159 | 7/1968 | Levine ............... 558/319 X |
| 3,433,823 | 3/1969 | McMahon et al. ....... 558/319 |
| 3,670,009 | 6/1972 | Taylor ................ 558/319 |
| 3,678,090 | 7/1972 | Taylor ................ 558/319 |
| 3,686,267 | 8/1972 | Taylor ................ 558/319 |
| 3,746,737 | 7/1973 | Tullman .............. 558/319 |
| 3,833,638 | 9/1974 | Knox et al. ........... 558/319 |
| 3,927,007 | 12/1975 | Lussling et al. ..... 558/319 X |
| 4,309,361 | 1/1982 | Suresh et al. ......... 558/319 |
| 4,760,159 | 7/1988 | Suresh et al. ......... 558/319 |
| 4,767,739 | 8/1988 | Glaeser et al. ..... 558/319 X |
| 4,783,545 | 11/1988 | Glaeser et al. ....... 558/319 |
| 4,801,568 | 1/1989 | Brazdil, Jr. et al. ... 502/209 |
| 4,801,727 | 1/1989 | Glaeser et al. ....... 558/319 |
| 4,814,478 | 3/1989 | Glaeser et al. ....... 558/319 |
| 4,866,024 | 9/1989 | Brazdil, Jr. et al. 558/319 X |
| 4,871,706 | 10/1989 | Brazdil, Jr. et al. ... 502/209 |
| 4,877,764 | 10/1989 | Glaeser et al. ..... 558/319 X |
| 4,883,896 | 11/1989 | Glaeser et al. ....... 558/319 |
| 4,888,438 | 12/1989 | Glaeser et al. ....... 558/319 |
| 5,008,427 | 4/1991 | Brazdil, Jr. et al. .... 558/319 |

FOREIGN PATENT DOCUMENTS

| | | |
|---|---|---|
| 0282314 | 9/1988 | European Pat. Off. ..... 558/319 |
| 0342777 | 11/1989 | European Pat. Off. . |
| 0344884 | 12/1989 | European Pat. Off. . |
| 2027238 | 9/1970 | France . |
| 2072334 | 9/1971 | France .. |
| A-2072399 | 9/1971 | France . |
| A-2119492 | 8/1972 | France . |
| 2119493 | 8/1972 | France . |
| 1336135 | 11/1973 | United Kingdom . |
| 1336136 | 11/1973 | United Kingdom . |
| 1337759 | 11/1973 | United Kingdom . |

OTHER PUBLICATIONS

Arzu B. Azimov, et al., *Journal of Catalysis*, "Dehydrogenation" Mechanism for Ammoxidation of Alkylaromatic Hydrocarbons, vol. 127, pp. 354–365 (1991).

Kim, et al., Chemistry Letters, 1989, pp. 2173–2176.

"Production of Acrylonitrile by Ammoxidation of Propane", Patent Abstracts of Japan, vol. 15, No. 206 (C-835), May 27, 1991.

*Primary Examiner*—Joseph Paul Brust
*Attorney, Agent, or Firm*—Burns, Doane, Swecker & Mathis

[57] ABSTRACT

The alkanes, e.g., propane, are selectively converted (ammoxidized) into admixtures comprising $\alpha,\beta$-unsaturated nitriles, e.g., acrylonitrile, by reacting same with ammonia and oxygen, in vapor phase, and in the presence of a catalytically effective amount of a solid catalyst, the catalytically active phase of which comprising (1) molybdenum, vanadium and oxygen and (2) at least one of the elements, manganese, zinc, cobalt, copper, lithium, sodium, potassium and silver.

16 Claims, 1 Drawing Sheet

CATALYTIC AMMOXIDATION OF SATURATED HYDROCARBONS

BACKGROUND OF THE INVENTION

1. Field of the Invention

The present invention relates to the ammoxidation of saturated hydrocarbons, and, more especially, to the conversion of alkanes into admixture comprising $\alpha,\beta$-unsaturated nitriles.

2. Description of the Prior Art

The ammoxidation of olefins is well known to this art, particularly of propylene. However, although the saturated hydrocarbons, which are more widely available, are more desirable starting materials from an economic standpoint, it is also well known to this art that these do not have a comparable reactivity in such type of reaction to form, especially, $\alpha,\beta$-unsaturated nitriles.

One of the difficulties encountered in the ammoxidation of saturated hydrocarbons is the requirement for catalysts suitable for dehydrogenating the saturated hydrocarbon under conditions which minimize or eliminate the combustion of the ammonia and/or that of the hydrocarbon while ensuring a reasonable selectivity, either to $\alpha,\beta$-unsaturated nitrile (target compound), for example to acrylonitrile starting from propane, or to enhanced value compounds (aforementioned nitrile and olefin), for example, to acrylonitrile and propylene starting from propane.

U.S. Pat. No. 3,365,482 describes the ammoxidation, especially of isobutane to methacrylonitrile, on a molybdenum-based catalyst deposited onto eta-alumina, doped with antimony at 508° C. starting from a gaseous mixture containing isobutane, air, ammonia and steam (1.0/4.5/1.0/12.5), the selectivity toward methacrylonitrile attaining a value of 49% for a degree of conversion of the isobutane of 22%.

Beginning with a propane/air/ammonia/steam (1.0/4.7/0.67/12.8) mixture, using the same catalyst and at 550° C., the selectivity toward acrylonitrile decreases to 15% for a degree of conversion of the propane of 29%.

French Patent 2,027,238 (corresponding in part to U.S. Pat. No. 3,670,009) describes a process for the ammoxidation, in vapor phase, of saturated hydrocarbons at a temperature greater than 500° C. on a solid catalyst, particularly of tin oxide, boron oxide, molybdenum oxide and silica. Thus, in Example IX of the Table on pages 12–13, the selectivity toward acrylonitrile attains a value of 35%, at 32% conversion of the propane, but under operating conditions wherein the propane/ammonia/air (1/1.2/12) reaction mixture is in the explosive region.

French Patent 2,072,334 (corresponding to British Patent No. 1,336,135) describes a process for the catalytic ammoxidation of alkanes in the vapor phase, at a temperature below 500° C. employing a high concentration of alkane in the gaseous feed mixture, on a solid catalyst, particularly of tin oxide and molybdenum oxide (90/10 by weight); however, better results are obtained using catalysts constituted of antimony oxide and vanadium oxide.

French Patent 2,072,399 describes a process for the catalytic ammoxidation of alkane, in the vapor phase, employing a high concentration of alkane in the gaseous feed mixture, on a solid catalyst which in particular is a binary mixture of oxides containing molybdenum oxide.

The following pairs are more particularly indicated: (Mo, Sb) (Mo, Sn) (Mo, V) (Mo, Ti) (Mo, Bi).

However, none of these pairs offers better results than those obtained using pairs which do not contain molybdenum. The yields of acrylonitrile obtained are very low; at best, 1.7% of the propane is converted to acrylonitrile at 570° C. using a catalyst based on the oxides of tin and titanium.

French Patent No. 2,119,492 (corresponding to U.S. Pat. No. 3,746,737 and to British Patent No. 1,337,759) describes the use of a binary composition based on the oxides of molybdenum and cerium. However, the results from the pair (Mo, Ce) appear poor in the absence of a halogen or halogenated compound.

It is also described to add to such binary composition (Mo, Ce) a third element selected from between tellurium and bismuth (cf. U.S. Pat. No. 3,833,638). Here again, the results of the catalytic system appear poor in the absence of a halogen or halogenated compound. Moreover, it will be appreciated that in the presence of $CH_3Br$, the selectivity toward acrylonitrile attains a value of 67% at a 98% conversion of the propane, but under operating conditions which establish the propane/ammonia/air (1/1.2/12) reaction mixture in the explosive region.

French Patent No. 2,119,493 describes carrying out the ammoxidation of alkanes in the vapor phase on a solid catalyst containing oxides of bismuth and molybdenum and, if appropriate, phosphorus and silica.

Here again, the results of the catalytic system appear poor in the absence of a halogen or halogenated compound and the reaction mixture is placed in the explosive region.

Because of the aforesaid disadvantages and drawbacks, considerable research, whether concurrent or subsequent, has been conducted on the use of solid catalysts based on vanadium and/or antimony.

In Chemistry Letters, 1989 (pp. 2173–2176) the ammoxidation of propane in the gas phase is described, using multicomponent metal oxides containing molybdenum and bismuth and having a structure of the type of that of scheelite. It appears that, despite the relatively moderate temperatures employed, the proportion of combustion products ($CO$, $CO_2$) is very high in all instances (at least 15%) and that certain catalytic compositions tested have very little activity with respect to the desired reaction, despite their use under conditions which are in the explosive region or very near such region.

Too, the presence of a halogenated compound can promote corrosion of the apparatus and is thus undesirable in an industrial process.

Moreover, it is apparent that the coproduction of large quantities of $CO$ and $CO_2$ is also undesirable on an industrial scale.

In addition, employing reaction mixtures which are in the explosive region is even less desirable on an industrial scale when the process is carried out in a stationary bed.

SUMMARY OF THE INVENTION

Accordingly, a major object of the present invention is the provision of an improved process for the ammoxidation of alkanes to obtain, with appreciable selectivity, a mixture of enhanced value compounds containing an $\alpha,\beta$-unsaturated nitrile, in particular acrylonitrile, while at the same time reducing, to as great an extent as is possible, the losses in starting material as a result of the formation of oxides of carbon.

Another object of this invention is the provision of an improved such process in which the solid catalyst is relatively simple to prepare and active in the absence of halogenated promoter and for gaseous mixtures which are not necessarily in the explosive region.

Briefly, the present invention features a process for the ammoxidation of alkanes in the vapor phase in the presence of a solid catalyst whose active phase contains molybdenum, vanadium and oxygen, said active phase also containing at least one other element selected from among manganese, zinc, cobalt, copper, lithium, sodium, potassium and silver.

DETAILED DESCRIPTION OF THE PREFERRED EMBODIMENTS OF THE INVENTION

More particularly according to the present invention, acyclic saturated hydrocarbons having from 3 to 12 carbon atoms per molecule are reacted in the vapor phase with ammonia and oxygen in the presence of a catalyst, the active phase of which will be more fully described below.

Indeed, in the subject process, it is possible to use diluent gases which are inert under the conditions of reaction, such as helium, nitrogen and argon. Likewise, steam can be added to the gaseous reaction mixture within wide limits. The reaction gas (saturated hydrocarbon, ammonia, oxygen) can thus be diluted with an inert diluent and/or with steam. In this respect, the content of steam can vary over wide limits, in particular from 0% to 50% and, preferably, from 3% to 30%. For good results, the content of reactive gas will be at least 3% and preferably at least 20%.

Within the reactive gas, the respective amounts of saturated hydrocarbon, ammonia and oxygen can vary over wide limits.

The amount of saturated hydrocarbon in the reactive gas preferably ranges from 5% to 70%. That of ammonia preferably ranges from 3% to 45% and that of oxygen preferably ranges from 3% to 45%.

Figure 1:
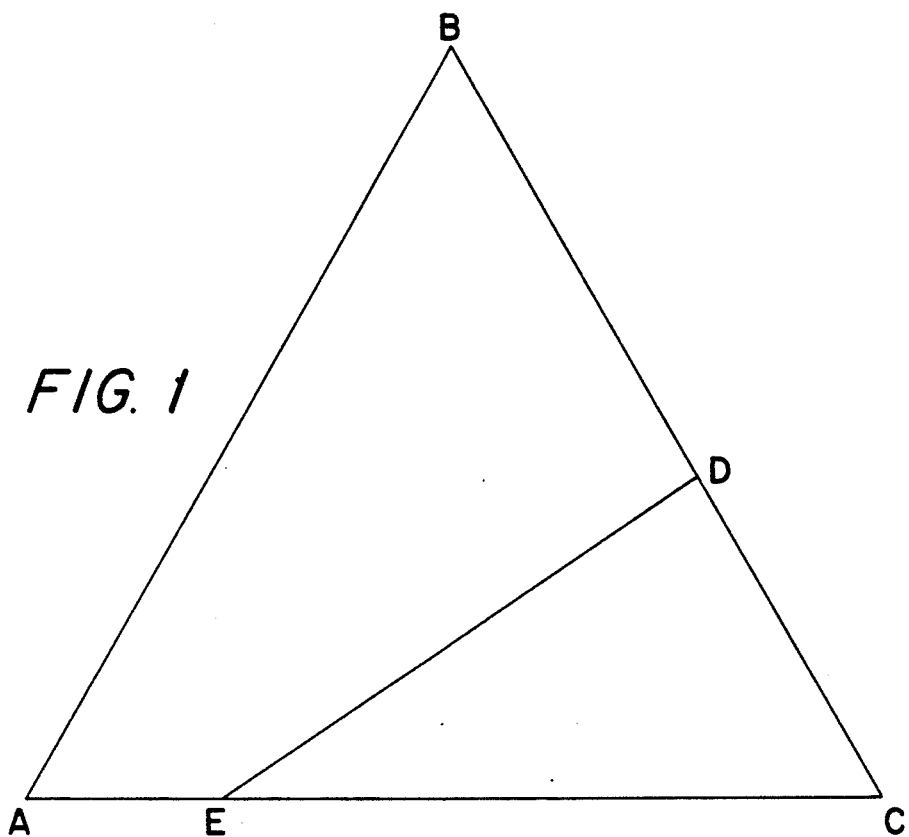

Also for good results, the composition of the reactive mixture will be outside the explosive region. As regards the ammoxidation of propane in the absence of an inert diluent, the composition (propane, oxygen, ammonia) is advantageously selected from within the quadrilateral ABDE shown in the ternary diagram ABC set forth in FIG. 1 of the Drawings.

In this ternary diagram, segment AB represents the ammonia content from 100% to 0%; segment BC represents the propane content from 100% to 0%; segment CA represents the oxygen content from 100% to 0%. Point D, situated inside segment BC, corresponds to a propane content of 45% in the binary system (propane/$O_2$); point E, situated inside segment AC, corresponds to an ammonia content of 79% in the binary system ($NH_3$/$O_2$).

Segment DE delimits the ternary diagram into two parts: a triangle CDE within which is situated the explosive region (determined at 1 bar and at 25° C.) and a quadrilateral ABDE within which the composition of the reactive gaseous mixture will advantageously be selected.

With respect to the ammoxidation of propane in the presence of inert diluent gas(es) and/or of steam, it is advisable to determine the composition of the ternary mixture (propane, oxygen and ammonia) in order to situate it on the aforesaid diagram, when the diluent gas and/or the steam is in low proportion.

Figure 2:
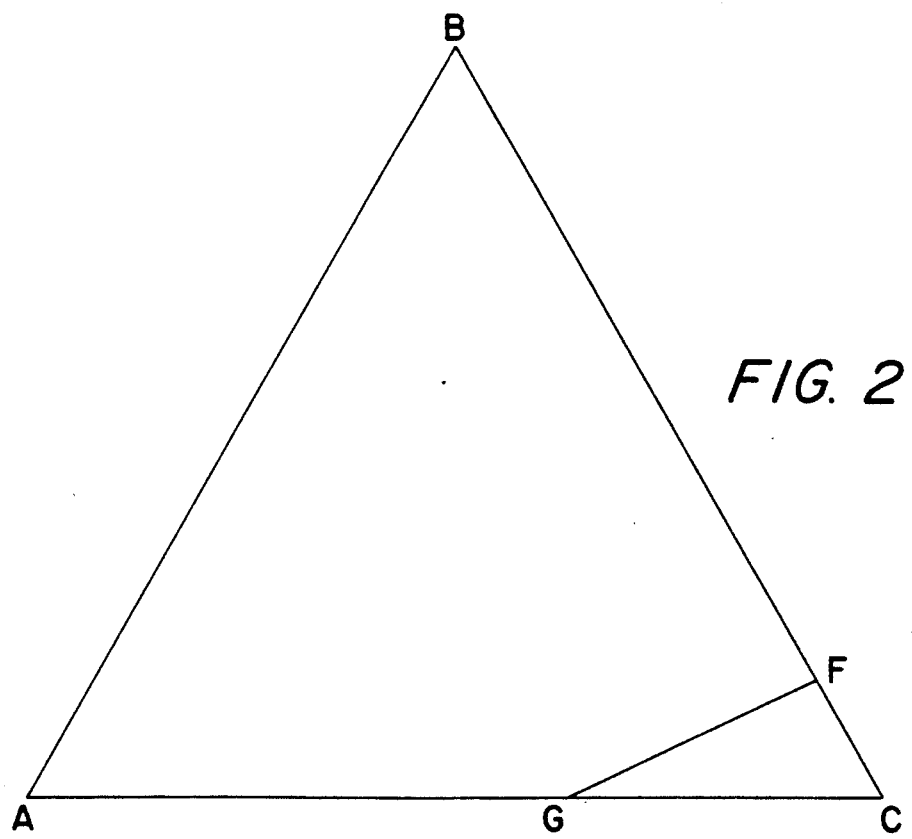

As regards the ammoxidation of propane by means of air as the oxygen source, the composition (propane, air and ammonia) will advantageously be selected inside the quadrilateral ABFG which appears within diagram ABC shown in FIG. 2.

In this second diagram, segment AB represents the ammonia content from 100% to 0%; segment BC represents the propane content from 100% to 0%; segment CA represents the air content from 100% to 0%. Point F, situated inside segment BC, corresponds to a propane content of 16% in the binary system (propane/air); point G, situated inside segment AC, corresponds to an ammonia content of 35% in the binary system (ammonia/air).

Segment FG delimits the ternary diagram into two parts: a triangle CFG within which is situated the explosive region (determined at 1 bar and at 550° C.) and a quadrilateral ABFG within which the composition of the reactive gaseous mixture will advantageously be selected.

This second diagram will be used in the event that the oxygen/diluent gas mixture corresponds to an oxygen content equivalent to that of the air ($\approx$21% oxygen) or in the event that this mixture is deficient in oxygen with respect to the air.

Starting from propane, a mixture will be obtained essentially consisting of propylene and acrylonitrile. Acrylonitrile is an intermediate produced industrially on a vast scale; propylene is a starting material traditionally used to produce acrylonitrile and various other intermediate compounds well known to this art.

Starting from isobutane, a mixture will be obtained containing methacrylonitrile and isobutene or n-butenes.

The process according to the invention is more particularly suitable for the ammoxidation of propane.

If the saturated hydrocarbon used is of technical grade, it will not contain significant amounts of ethylenically unsaturated compounds. Thus, the propane involved will only contain trace amounts of propylene.

The process according to the invention is carried out as a vapor phase reaction. Consequently, any apparatus suitable for carrying out ammoxidation or oxidation reactions in the vapor phase can be used. The process can be carried out continuously or discontinuously, in either a stationary bed or a fluidized bed.

The reaction temperature generally ranges from 350° to 550° C. and, preferably, from 410° to 510° C.

The total pressure of the reaction mixture can be greater than or equal to atmospheric pressure. It generally ranges from 1 to 6 bar and, preferably, from 1 to 4 bar.

The gas flow rate is established such that the hourly volume rate ranges from 100 to 36,000 $h^{-1}$ and, preferably, from 200 to 20,000 $h^{-1}$.

Of Course, one skilled in this art can readily determine a compromise between the temperature, the gas flow rate, the precise nature of the catalyst used and the various other parameters of the reaction, taking account of the production objectives.

In the process according to the present invention, a solid catalyst is used whose active phase contains molybdenum, vanadium and oxygen, said active phase also containing at least one other element selected from among manganese, zinc, cobalt, copper, lithium, sodium, potassium and silver.

The preferred active phases of the catalysts of the present invention correspond to the empirical formula:

$$Mo_aV_bM_cO_x$$

in which M represents one or more elements selected from among manganese, zinc, cobalt, copper, lithium, sodium, potassium and silver; a is a number greater than zero and less than 2; b is a number greater than zero and less than 2; c is a number greater than zero and less than 1; x is determined by the oxidation number of the other elements.

Preferably, M represents one or more elements, at least one of which is selected from among manganese, zinc and cobalt.

Preferably, in said empirical formula:
a ranges from 0.1 to 1, inclusive;
ranges from 0.05 to 1.8, inclusive; and
ranges from 0.1 to 1, inclusive.

More particularly preferred are active phases having said empirical formula and in which:
M represents an element selected from among manganese, zinc and cobalt
ranges from 0.1 to 1, inclusive;
ranges from 0.05 to 1.8, inclusive; and
ranges from 0.01 to 1, inclusive.

The active phases can be employed in the bulk form or in the particulate state. These phases can be in the form of powders or beads, extruded or crushed, for example.

They can also be deposited onto an inert support or coated thereon. The nature of the support is not critical so long as it is chemically inert with respect to the reactants under the reaction conditions selected. Exemplary supports suitable for the preparation of catalyst which can be used in the process according to the invention include silica, alumina, silica/alumina, sintered clay, carborundum, magnesia, magnesium silicate and diatomaceous earth. Such support is preferably nonporous and can, especially, be based on a refractory oxide in the particulate state, the most typical support being clay-based. This support can, for example, be constituted of inert, complete, solid and rough clay beads having a diameter ranging from 0.5 to mm. The precise value of the diameter of the beads will be selected as a function of the acceptable pressure decrease in the reactor. The support can also be made nonporous by enamelling.

The support can also be a ceramic substrate, such substrate preferably being in the form of an inert and rigid structure of monolithic type comprising channels or ducts. These supports are well known to this art and are widely described in the literature. The substrates used which are fabricated from a ceramic substance are especially those containing, principally, cordierite, alumina, mullite, porcelain, and the carbides of boron or silicon.

When a coated catalyst is used, the amount of active phase, which can vary over wide limits, typically ranges from 5% to 35% and, preferably, from 8% to 20% by weight with respect to the entire catalyst (support + active phase).

The catalysts can be prepared according to any known technique, such as mixing suitable salts of the constituent elements in water or in another solvent followed by evaporation to dryness, or by precipitation by addition of a base such as aqueous ammonia or an acid such as hydrochloric acid, or by atomization of a suspension obtained after mixing suitable salts.

The most commonly employed suitable salts are soluble in water and contain anions and cations which can be decomposed by heat during subsequent stages. These include, for example, ammonium heptamolybdate for molybdenum, ammonium vanadate for vanadium, and the nitrates or chlorides of manganese, zinc and cobalt.

Once the mixture of the salts is prepared, a precursor can be obtained by the so-called evaporation technique. The water of the suspension is evaporated by heating at a temperature of from 20° to 100° C. with stirring for the time period necessary to produce a nonflowing paste. Stirring and heating are then terminated.

The paste thus obtained, spread out over a thickness of approximately 2 cm, is dried in air at approximately 120° C. for approximately 15 hours. The precursor thus produced can then be crushed and calcined at a temperature of from 200 to 1,000° C. preferably from 400° to 600° C., for at least 30 min, preferably at least one hour. It can prove useful to conduct several crushing and calcination operations successively. The calcination can be carried out while progressively increasing the temperature, 100° to 200° C. per hour for example, especially because of the risks associated with the exothermic decomposition of ammonium nitrate at about 230° C. The active phase thus obtained after cooling can then be crushed such that its particle size does not exceed approximately 400 μm.

The precursor can also be obtained via precipitation by addition, for example, of aqueous ammonia or hydrochloric acid at the end of mixing of the salts to stabilize the pH at approximately 7. It is preferable to heat the suspension at a temperature of from 20° to 100° C. for approximately one hour to complete the precipitation of the species.

The suspension is then filtered and washed. The filter cake is subsequently spread out and then dried, crushed and calcined under the conditions indicated above in the context of the evaporation technique, to provide the active phase. Several active phases can be admixed to obtain a new active phase, for example in a mortar.

Certain catalysts useful for conducting the subject process in a stationary bed are produced by coating the crushed, intermediate or final product active phases in a manner per se known to this art. Such conventional technique entails depositing a layer of intermediate or finished active phase around inert but rough spheres (beads).

Once the beads are coated with the desired amount of the active phase, they are dried with hot air at a temperature ranging from 70° to 150° C. for at least 30 minutes and then introduced into an oven, wherein they are calcined at a temperature ranging from 300° to 600° C. preferably from 450° to 500° C. for at least 3 hours.

Certain catalysts which are useful for carrying out the process according to the invention in a moving bed or fluidized bed can be prepared via the technique, also per se known to this art, of drying by atomization, in a preferably nonreducing atmosphere. By such an operation, followed, if appropriate, by calcination at a temperature on the order of 400° C. to 1,100° C., powders are obtained which are spherical in shape and have a diameter ranging from 5 to 700 μm. Powders comprising at least 80% by weight of particles having sizes ranging from 5 to 100 μm are preferred for fluidized bed applications.

The products of the reaction can be recovered from the effluent gases by any suitable means. For example, the effluent gases can be transferred into a condenser containing dilute sulfuric acid to neutralize the unreacted ammonia. The gases can then be passed through a refrigerated absorbing column to condense the acrylonitrile, acetonitrile and hydrocyanic acid, the uncondensed vapors containing, principally, unreacted propane, propylene, light hydrocarbons and, if appropriate, $CO_2$. The acrylonitrile and hydrocyanic acid can then be separated from the acetonitrile by distillation and the acrylonitrile/hydrocyanic acid mixture thus recovered can then be distilled, in turn, to separate the acrylonitrile from the hydrocyanic acid.

In order to further illustrate the present invention and the advantages thereof, the following specific examples are given, it being understood that same are intended only as illustrative and in nowise limitative.

EXAMPLE 1

Preparation of a catalyst (A), the active phase of which having the formula $Mn_{0.8}V_{1.6}Mo_{0.4}O_6$ An active phase of composition $Mn_{0.8}V_{1.6}Mo_{0.4}O_6$ was prepared according to the following procedure:

A solution (a) of manganese nitrate was prepared by dissolving 204.91 g of 98% $Mn(NO_3)_2 \cdot 4H_2O$ (marketed by Prolabo) in 300 cm$^3$ of demineralized water, a solution (b) of ammonium heptamolybdate was prepared by dissolving 70.64 g of $(NH_4)_6Mo_7O_{24} \cdot 4H_2O$ (marketed by Merck) in 200 cm$^3$ of demineralized water, and a suspension (c) was prepared of 187.17 g of $NH_4VO_3$ (marketed by Prolabo) in 400 cm$^3$ of demineralized water. The solution (a) was poured into the suspension (c) in a stirred reactor. The solution (b) was then introduced with continuous stirring. The mixture was stirred vigorously and the temperature was progressively increased to 100°–110° C. The paste obtained was dried at 120° C. for approximately 15 hours. The product obtained was then crushed, calcined at 600° C. for 6 hours and recrushed and recalcined at 600° C. for 42 hours.

The product (I) thus obtained had a specific surface, measured according to the B.E.T. technique, of 0.1 $m^2g^{-1}$.

20 g of product (I) were slowly dusted over 123 g of inert support constituted by clay beads having a mean diameter of 4.8 mm, placed beforehand in a rotary coating device and moistened with 10% aqueous glucose solution. As soon as the beads were dry on the outside, a small amount of the glucose solution was sprayed thereon. The product (I) was then again dusted onto the beads. These operations were continued alternately until all the product (I) had been coated thereon. Drying was then carried out at 120° C. for 2 hours and calcining at 480° C. for 6 hours.

The catalyst (A) thus obtained, in accordance with the invention, comprised 11.6% by weight of $Mn_{0.8}V_{1.6}Mo_{0.4}O_6$ deposited on to clay beads.

EXAMPLE 2

Preparation of a catalyst (B), the active phase of which having the formula $Mn_{0.8}V_{1.6}Mo_{0.4}O_6$ An active phase of composition $Mn_{0.8}V_{1.6}Mo_{0.4}O_6$ was prepared according to the same procedure as in Example 1, except for the final calcinations which were carried out in the following manner: the product was crushed, calcined at 450° C. for 8 hours, recrushed, recalcined at 450° C. for 8 hours, recrushed, calcined at 550° C. for 4 hours, and recrushed and recalcined at 550° C. for 4 hours.

The product (I) thus obtained had a specific surface, measured according to the B.E.T. technique, of 1.7 $m^2g^{-1}$.

20 g of product (I) were slowly dusted onto 123 g of inert support constituted of clay beads having a mean diameter of 4.8 mm, placed beforehand in a rotary coating device and moistened with 10% aqueous glucose solution. As soon as the beads were dry on the outside, a small amount of the glucose solution was sprayed thereon. The product (I) was then dusted again onto the beads. These operations were continued alternately until all the product (I) had been coated thereon. Drying was then carried out at 120° C. for 2 hours and calcining at 480° C. for 6 hours.

The catalyst (B) thus obtained, in accordance with the invention, comprised 10% by weight of $Mn_{0.8}V_{1.6}Mo_{0.4}O_6$ deposited onto clay beads.

EXAMPLE 3

Preparation of a catalyst (C), the active phase of which having the formula $Zn_{0.85}V_{1.7}Mo_{0.3}O_6$ An active phase of composition $Zn_{0.85}V_{1.7}Mo_{0.3}O_6$ was prepared according to the following procedure:

A solution (a) of zinc nitrate was prepared by dissolving 252.8 g of $Zn(NO_3)_2 \cdot 6H_2O$ (marketed by Prolabo) in 250 cm$^3$ of demineralized water, a solution (b) of ammonium heptamolybdate was prepared by dissolving 52.95 g of $(NH_4)_6Mo_7O_{24} \cdot 4H_2O$ (marketed by Merck) in 150 cm$^3$ of demineralized water, and a suspension (c) was prepared of 165.75 g of $NH_4VO_3$ (marketed by Prolabo) in 210 cm$^3$ of demineralized water.

The two solutions (a) and (b) were mixed and this mixture was poured into the suspension (c) in a stirred reactor. The mixture was maintained under stirring for 20 hours and the temperature was progressively increased to 100°–110° C. The mixture was maintained at reflux for 1 hour and evaporated. The paste obtained was dried at 120° C. for approximately 15 hours. The product obtained was then crushed, calcined at 250° C. for 4 hours, recrushed and calcined at 450° C. at 8 hours, recrushed and recalcined at 450° C. for 8 hours, recrushed and calcined at 550° C. for 4 hours, and recrushed and recalcined at 550° C. for 4 hours.

The product (I) thus obtained had a specific surface, measured according to the B.E.T. technique, of 0.8 $m^2g^{-1}$.

20 g of product (I) were slowly dusted onto 123 g of inert support constituted of clay beads having mean diameter of 4.8 mm, placed beforehand in a rotary coating device and moistened with 10% aqueous glucose solution. As soon as the beads were dry on the outside, a small amount of the glucose solution was sprayed thereon. The product (I) was then dusted again onto the beads. These operations were continued alternately until all the product (I) had been coated thereon. Drying was then carried out at 120° C. for 2 hours and calcining at 480° C. for 6 hours.

The catalyst (C) thus obtained, in accordance with the invention, comprised 12% by weight of $Zn_{0.85}V_{1.7}Mo_{0.3}O_6$.

EXAMPLE 4

Preparation of a catalyst (D), the active phase of which having the formula $Co_{0.9}V_{1.8}Mo_{0.2}O_6$ An active phase of composition $Co_{0.9}V_{1.8}Mo_{0.2}O_6$ was prepared in the following manner: 84 g of $NH_4VO_3$ were suspended in 100 cm$^3$ of demineralized water, a solution of ammonium heptamolybdate was prepared by dissolving 14 g of $(NH_4)_6Mo_7O_{24}\cdot 4H_2O$ in 100 cm$^3$ of demineralized water and a solution of cobalt nitrate was prepared by dissolving 105 g of $Co(NO_3)_2\cdot 6H_2O$ in 100 cm$^3$ of demineralized water.

The solution of ammonium heptamolybdate was introduced into the suspension of ammonium metavanadate in a stirred reactor. The solution of cobalt nitrate was then introduced with continuous stirring. After stirring for 20 hours at room temperature, the mixture was evaporated to dryness and the residue was dried at 120° C. and then calcined at 250° C. for 4 hours. The product obtained was crushed and was subjected to the following calcinations/crushings cycle:

450° C. for 4 hours/crushing,
450° C. for 4 hours/crushing,
450° C. for 8 hours/crushing,
550° C. for 4 hours/crushing,
550° C. for 4 hours/crushing, The product (I) thus prepared had a specific surface, measured according to the B.E.T. technique, of 2 m$^2$g$^{-1}$.

15 g of product (I) were slowly dusted onto 100 g of inert support constituted of clay beads having a mean diameter of 4.8 mm, placed beforehand in a rotary coating device and moistened with 10% aqueous glucose solution. As soon as the beads were dry on the outside, a small amount of glucose solution was sprayed thereon. The product (I) was then dusted again onto the beads. These operations were continued alternately until all the product (I) had been coated thereon. Drying was then carried out at 120° C. for 2 hours and calcining at 480° C. for 6 hours.

The catalyst (D) thus obtained, in accordance with the invention, comprised 12% by weight of $Co_{0.9}V_{1.8}Mo_{0.2}O_6$ deposited onto clay beads.

EXAMPLE 5

Preparation of a catalyst (E), the active phase of which having the formula $Mn_{0.8}V_{1.6}Mo_{0.4}O_6$ A product (I) of composition $Mn_{0.8}V_{1.6}Mo_{0.4}O_6$, was prepared according to the following procedure:

A solution (a) of manganese nitrate was prepared by dissolving 153.7 g of $Mn(NO_3)_2\cdot 4H_2O$ in 225 cm$^3$ of demineralized water, a solution (b) of ammonium heptamolybdate was prepared by dissolving 141.28 g of $(NH_4)_6Mo_7O_{24}\cdot 4H_2O$ in 400 cm$^3$ of demineralized water, and a suspension (c) was prepared of 140 g of $NH_4VO_3$ in 150 cm$^3$ of demineralized water.

The mixture of solutions (a) and (b) was poured into suspension (c) in a stirred reactor. The mixture was stirred for about twenty hours and the temperature was progressively increased to 100°-110° C. The paste obtained was dried at 120° C. for approximately 15 hours. The product was calcined under air at 250° C. for 4 hours, crushed, calcined at 450° C. for 8 hours, recrushed, recalcined at 450° C. for 8 hours, recrushed, calcined at 550° C. for 4 hours, and recrushed and recalcined at 550° C. for 4 hours.

A product (II), of composition $\alpha MnV_2O_6$, was then prepared according to the procedure described by R. Kozlowski, J. Ziolkowski, K. Mocala & J. Haber, *J. Sol. State Chem.*, 35, 1–9 (1980), i.e., a solution of manganese nitrate was prepared by dissolving 256.13 g of $Mn(NO_3)_2\cdot 4H_2O$ in 300 cm$^3$ of demineralized water. 116.98 g of $NH_4VO_3$ were suspended in 200 cm$^3$ of demineralized water. The manganese nitrate solution was poured into the ammonium metavanadate suspension in a stirred reactor. After stirring for 10 to 15 min at room temperature, the solid was filtered off on sintered glass and washed with 2 liters of demineralized water. The product obtained was then dried at 120° C. for approximately 15 hours and then calcined under air for 5 hours at 500° C.

15 g of product (I) and 15 g of product (II) thus obtained were mixed in a mortar.

The product (III) thus prepared, of overall composition $Mn_{0.8}V_{1.6}Mo_{0.4}O_6$, had a specific surface, measured according to the B.E.T. technique, of 3 m$^2$g$^{-1}$.

10 g of product (III) were slowly dusted onto 67 g of inert support constituted of clay beads having a mean diameter of 4.8 mm, placed beforehand in a rotary coating device and moistened with 10% aqueous glucose solution. As soon as the beads were dry on the outside, a small amount of the glucose solution was sprayed thereon. Product (III) was then dusted again onto the beads. These operations were continued alternately until all the product (III) had been coated thereon. Drying was then carried out at 120° C. for 2 hours and calcining at 480° C. for 6 hours.

The catalyst (E) thus obtained, in accordance with the invention, comprised 12.4% by weight of $Mn_{0.8}V_{1.6}Mo_{0.4}O_6$ deposited onto clay beads.

EXAMPLE 6

Preparation of a catalyst (F), the active phase of which having the formula $Mn_{0.4}V_{0.05}Mo_{0.4}O_{1.75}$ A product (I) of composition $Mn_{0.4}V_{0.05}Mo_{0.4}O_{1.75}$ was prepared according to the following procedure:

A solution (a) of manganese chloride was prepared by dissolving 79.16 g of $MnCl_2\cdot 4H_2O$ in 300 cm$^3$ of demineralized water, and a solution (b) of ammonium heptamolybdate was prepared by dissolving 70.6 g of $(NH_4)_6Mo_7O_{24}\cdot 4H_2O$ in 300 cm$^3$ of demineralized water.

4.52 g of $V_2O_5$ and then solution (b) were added to solution (a) in a stirred reactor. 40 cm$^3$ of $NH_4OH$ (20% $NH_3$) were then added and the mixture was heated at reflux for 3 hours. The solid was filtered off on sintered glass and washed with 1 l of demineralized water. The product obtained was then dried at 120° C. for approximately 15 hours and then calcined under air at 500° C. for 4 hours.

10 g of product (I) thus obtained were slowly dusted onto 67 g of inert support constituted of clay beads having a mean diameter of 4.8 mm, placed beforehand in a rotary coating device and moistened with 10% aqueous glucose solution. As soon as the beads were dry on the outside, a small amount of the glucose solution was sprayed thereon. Product (I) was then dusted again onto the beads. These operations were continued alternately until all the product (I) had been coated thereon. Drying was then carried out at 120° C. for 2 hours and calcining at 480° C. for 6 hours.

The catalyst (F) thus obtained, in accordance with the invention, comprised 9.1% by weight of $Mn_{0.4}V_{0.05}Mo_{0.4}O_{1.75}$ deposited onto clay beads.

COMPARATIVE EXAMPLE (a): a. ),:

Preparation of a catalyst (a) not according to the invention and the active phase of which having the formula $MnV_2O_6$ Product (II) prepared in Example 5 above had a specific surface, measured according to the B.E.T. technique, of 5 $m^2g^{-1}$. This product is designated product (I) in the present example.

20 g of product (I) were slowly dusted onto 123 g of inert support constituted of clay beads having a mean diameter of 4.8 mm, placed beforehand in a rotary coating device and moistened with 10% aqueous glucose solution. As soon as the beads were dry on the outside, a small amount of the glucose solution was sprayed thereon. Product (I) was then dusted again onto the beads. These operations were continued alternately until all the product (I) had been coated thereon. Drying was then carried out at 120° C. for 2 hours and calcining at 480° C. for 6 hours.

The catalyst (a) thus obtained, not in 15 accordance with the invention, comprised 13% by weight of $\alpha Mn\text{-}V_2O_6$ deposited on to clay beads.

COMPARATIVE EXAMPLE (b)

Preparation of a catalyst (b) not according to the invention and the active phase of which having the formula $ZnV_2O_6$ A solution of zinc nitrate was prepared by dissolving 148.7 g of $Zn(NO_3)_2 \cdot 6H_2O$ (marketed by Prolabo) in 200 $cm^3$ of demineralized water. 117 g of $NH_4VO_3$ (marketed by Prolabo) were suspended in 200 $cm^3$ of demineralized water. The zinc nitrate solution was poured into the ammonium metavanadate suspension in a stirred reactor. After stirring for 23 hours at room temperature, the solid was filtered off on sintered glass and washed with 400 $cm^3$ of demineralized water. The product obtained was then dried at 120° C. for approximately 15 hours and then calcined under air for 5 hours at 500° C.

The product (I) thus obtained had a specific surface, measured according to the B.E.T. technique, of 3 $m^2g^{-1}$.

20 g of product (I) were slowly dusted onto 123 g of inert support constituted of clay beads having a mean diameter of 4.8 mm, placed beforehand in a rotary coating device and moistened with 10% aqueous glucose solution. As soon as the beads were dry on the outside, a small amount of the glucose solution was sprayed thereon. Product (I) was then dusted again onto the beads. These operations were continued alternately until all the product (I) had been coated thereon. Drying was then carried out at 120° C. for 2 hours and calcining at 480° C. for 6 hours.

The catalyst (b) thus obtained, not in accordance with the invention, comprised 16% by weight of $ZnV_2O_6$ deposited onto clay beads.

COMPARATIVE EXAMPLE (c)

Preparation of a catalyst (c) not according to the invention and the active phase of which having the formula $CoV_2O_6$ An active phase of composition $CoV_2O_6$ was prepared in the following manner:

117 g of $NH_4VO_2$ were suspended in 200 $cm^3$ of demineralized water and a solution of cobalt nitrate was prepared by dissolving 145.5 g of $Co(NO_3)_2 \cdot 6H_2O$ in 200 $cm^3$ of demineralized water.

The cobalt nitrate solution was introduced into the ammonium metavanadate suspension in a stirred reactor. After stirring for 23 hours at room temperature, the solid was filtered off on sintered glass and washed 3 times with 200 $cm^3$ of demineralized water. The product obtained was then dried at 120° C. for approximately 15 hours and then calcined under air for 5 hours at 500° C.

The product (I) thus prepared had a specific surface, measured according to the B.E.T. technique, of 3.6 $m^2g^{-1}$.

15 g of product (I) were slowly dusted onto 100 g of inert support constituted of clay beads having a mean diameter of 4.8 mm, placed beforehand in a rotary coating device and moistened with 10% aqueous glucose solution. As soon as the beads were dry on the outside, a small amount of glucose solution was sprayed thereon. Product (I) was then dusted again onto the beads. These operations were continued alternately until all the product (I) had been coated thereon. Drying was then carried out at 120° C. for 2 hours and calcining at 480° C. for 6 hours.

The catalyst (c) thus obtained, not in accordance with the invention, comprised 12% by weight of $CoV_2O_6$ deposited onto clay beads.

General Procedure For Ammoxidation Tests

The catalyst sample was heated beforehand to a temperature of 150° C. on a test bench while purging with helium for 10 min, and it was then subjected to a gas flow whose composition will be specified for each Example and which contained propane, ammonia, oxygen, steam and helium.

The total pressure of the reaction mixture was 1.3 bar abs.

The gas flow rate was defined such as to provide an hourly volume rate (HVR) of 1,000 $h^{-1}$, except where otherwise indicated.

The principle of the ammoxidation test for propane was the following:

(i) The catalyst was heated to a temperature $T_1$, for example 300° C., and, after stabilizing it for 30 min at the temperature $T_1$, the composition of the mixture at the reactor outlet was determined by gas phase chromatography;

(ii) The conversion percentages and the selectivities obtained on the catalyst examined at the inlet temperature $T_1$ were calculated using relationships of the type:

Conversion of propane = % converted propane/% propane introduced

Selectivity toward acrylonitrile = % propane converted to acrylonitrile/% converted propane;

(iii) The catalyst was then heated from 300° to 550° C. by increments of 20° to 30° C. and the conversion percentages and the selectivities were determined every 40 min.

In the Examples below, the following conventions are employed:

| | |
|---|---|
| DC(C$_3$H$_8$) = | conversion of propane, |
| S(ACN) = | selectivity toward acrylonitrile, |
| S(ACN + C$_3$H$_6$) = | selectivity toward acrylonitrile and propylene, |
| S(CO$_x$) = | selectivity toward carbon monoxide and carbon dioxide. |

EXAMPLE 7/COMPARATIVE EXAMPLE (d)

The results using catalysts (A) and (a) were determined at various temperatures and under the following common conditions:

Catalyst volume (active phase+clay beads)=20 cm$^3$,
Total flow rate of the synthetic mixture=20 l.h$^{-1}$,
Composition of the mixture:

| | |
|---|---|
| C$_3$H$_8$ = | 19.0% (% by volume) |
| NH$_3$ = | 7.5% |
| O$_2$ = | 10.0% |
| H$_2$O = | 25.0% |
| He = | 38.5% |

The results obtained and the specific conditions are reported in Table I below:

TABLE I

| EX-AM-PLE | CAT-A-LYST | T (°C.) | DC(C$_3$H$_8$) (%) | S(ACN) (%) | S(ACN + C$_3$H$_6$) (%) | S(CO$_x$) (%) |
|---|---|---|---|---|---|---|
| (d) | (a) | 420 | 11 | 12 | 34 | 22 |
| | | 445 | 12 | 2.5 | 35 | 27 |
| | | 470 | 15 | 0 | 37 | 31 |
| 7 | (A) | 420 | 2 | 8 | 79 | 0 |
| | | 470 | 11 | 25 | 63 | 2 |
| | | 510 | 19 | 29 | 58 | 11 |

EXAMPLE 8/COMPARATIVE EXAMPLE (e)

The results obtained using catalysts (C) and (b) were determined at 480° C. and under the following common conditions:

Catalyst volume (active phase+clay beads)=cm$^3$,
Total flow rate of the synthetic mixture=25 l.h$^{-1}$,
Composition of the mixture:

| | |
|---|---|
| C$_3$H$_8$ = | 20.0% (% by volume) |
| NH$_3$ = | 5.0% |
| O$_2$ = | 15.0% |
| H$_2$O = | 20.0% |
| He = | 40.0% |

The results obtained and the specific conditions are reported in Table II below:

TABLE II

| EX-AM-PLE | CATALYST | DC(C$_3$H$_8$) (%) | S(ACN) (%) | S(ACN + C$_3$H$_6$) (%) | S(CO$_x$) (%) |
|---|---|---|---|---|---|
| (e) | (b) | 14 | 0 | 44 | 39 |
| 8 | (C) | 9 | 10 | 38 | 17 |

EXAMPLE 9/COMPARATIVE EXAMPLE (f)

The results-obtained using catalysts (D) and (c) were determined at various temperatures and under the following common conditions:

Catalyst volume (active phase+clay beads)=cm$^3$,
Total flow rate of the synthetic mixture=25 l.h$^{-1}$,
Composition of the mixture:

| | |
|---|---|
| C$_3$H$_8$ = | 7.5% (% by volume) |
| NH$_3$ = | 15.0% |
| O$_2$ = | 15.0% |
| H$_2$O = | 20.0% |
| He = | 42.5% |

The results obtained and the specific conditions are reported in Table III below:

TABLE III

| EX-AM-PLE | CAT-A-LYST | T (°C.) | DC(C$_3$H$_8$) (%) | S(ACN) (%) | S(ACN + C$_3$H$_6$) (%) | S(CO$_x$) (%) |
|---|---|---|---|---|---|---|
| (f) | (c) | 415 | 4 | 1 | 89 | 1 |
| | | 435 | 9 | 2 | 57 | 25 |
| | | 455 | 19 | 0 | 26 | 31 |
| 9 | (D) | 415 | 5 | 12 | 78 | 0 |
| | | 435 | 8 | 8 | 72 | 9 |
| | | 455 | 16 | 18 | 51 | 16 |

EXAMPLES 10 TO 21

The results obtained using various catalysts, the preparation of which was described in Examples 1 to 6 above, were determined under various conditions at an hourly volume rate (HVR) of 1,000 h$^{-1}$.

The reference to the catalyst used, the specific conditions employed, as well as the results obtained, are reported in Table IV below:

TABLE IV

| Reference | Example 10 | | | Example 11 | | | Example 12 | | | Example 13 | | | Example 14 | | | Example 15 |
|---|---|---|---|---|---|---|---|---|---|---|---|---|---|---|---|---|
| CATALYST | (A) | | | (B) | | | (A) | | | (B) | | | (D) | | | (E) |
| Composition(*) | % Volume | | | % Volume | | | % Volume | | | % Volume | | | % Volume | | | % Volume |
| C$_3$H$_8$ | 11 | 19 | 26 | 20 | | | 19 | | | 20 | | | 40 | | | 48 |
| NH$_3$ | 7.5 | | | 5 | 15 | 25 | 7.5 | | | 15 | | | 15 | | | 9 |
| O$_2$ | 10 | | | 15 | | | 4 | 10 | 16.5 | 5 | 15 | 25 | 15 | | | 18 |
| H$_2$O | 25 | | | 20 | | | 25 | | | 20 | | | 20 | | | 20 |
| He | qs 100% | | | qs 100% | | | qs 100% | | | qs 100% | | | 10 | | | 5 |
| T(°C.) | 470 | | | 460 | | | 470 | | | 460 | | | 440 | 460 | 480 | 430 |
| % | | | | | | | | | | | | | | | | |
| DC(C$_3$H$_8$) | 9 | 11 | 3 | 11 | 11 | 11 | 6 | 11 | 12 | 5 | 11 | 7 | 15 | 14 | 14 | 8 |
| S(ACN) | 18 | 25 | 7 | 20 | 14 | 8 | 16 | 25 | 21 | 14 | 14 | 7 | 22 | 22 | 27 | 14 |
| S(ACN + C$_3$H$_6$) | 65 | 63 | 88 | 59 | 48 | 47 | 78 | 63 | 54 | 81 | 48 | 68 | 57 | 60 | 64 | 63 |
| S(CO$_x$) | 8 | 2 | 0 | 0 | 0 | 5 | 2 | 12 | 0 | 0 | 0 | 0 | 0 | 0.2 | 0 | 6 |
| Reference | | | | Example 16 | | | Example 17 | | | Example 18 | | | Example 19 | | | Example 20 | Example 21 |

TABLE IV-continued

| CATALYST Composition(*) | (E) % Volume | (F) % Volume | (D) % Volume | (D) % Volume | (F) % Volume | (F) % Volume |
|---|---|---|---|---|---|---|
| C₃H₈ | | 40 | 25 | 25 | 25 | 7.5 |
| NH₃ | | 15 | 10 | 25 | 10 | 15 |
| O₂ | | 15 | 25 | 10 | 25 | 15 |
| H₂O | | 20 | 20 | 20 | 20 | 20 |
| He | | 10 | 20 | 20 | 20 | 42.5 |
| T(°C) | 450   470 | 480 | 420 | 440   460 | 440   460 | 460   480 |
| % | | | | | | |
| DC(C₃H₈) | 8   9 | 10 | 12 | 5   5 | 5   10 | 13   17 |
| S(ACN) | 12   12 | 18 | 18 | 11   10 | 10   19 | 22   26 |
| S(ACN + C₃H₆) | 62   64 | 69 | 51 | 77   79 | 72   61 | 52   54 |
| S(COₓ) | 5   9 | 4 | 0 | 0   0 | 0   4 | 0   0 |

(*)of the gas mixture

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the ammoxidation of a saturated hydrocarbon into an α,β-ethylenically unsaturated nitrile, by reacting an acyclic alkane containing at least 3 carbon atoms per molecule with ammonia and oxygen, in vapor phase, and in the presence of a catalytically effective amount of a solid catalyst, said catalyst having an active phase represented by the empirical formula (I):

$$Mo_a V_b M_c O_x \qquad (I)$$

in which M is one or more of the elements, manganese, zinc, cobalt, copper, lithium, sodium, potassium, and silver; a is a number greater than zero and less than 2; b is a number greater than zero and less than 2; c is a number greater than zero and less than 1; and x is determined by the oxidation number of the other elements thereof and said active phase represented by formula (I) being the sole ammoxidation catalytic component.

2. The process as defined in claim 1, wherein the selectively toward the production of carbon oxides is lower than that obtained with the same catalyst but free of Mo under the same reaction conditions.

3. The process as defined by claim 1, wherein said empirical formula, at least one of the elements M is manganese, zinc or cobalt.

4. The process as defined by claim 1, wherein said empirical formula a is a number ranging from 0.1 to 1, b is a number ranging from 0.05 to 1.8, c is a number ranging from 0.1 to 1.

5. The process as defined by claim 1, wherein said empirical formula M is manganese, zinc or cobalt; a is a number ranging from 0.1 to 1; b is a number ranging from 0.05 to 1.8; and c is a number ranging from 0.1 to 1.

6. The process as defined by claim 1, said alkane comprising propane.

7. The process as defined by claim 1, carried out in the presence of steam.

8. The process as defined by claim 1, carried out at a temperature ranging from 350° C. to 550° C.

9. The process as defined by claim 1, carried out at a total pressure ranging from 1 to 6 bar.

10. The process as defined by claim 1, carried out at an hourly space velocity ranging from 100 to 36,000 h⁻¹.

11. The process as defined by claim 1, the reactive gas comprising from 5% to 70% of said alkane, from 3% to 45% of ammonia and from 3% to 45% of oxygen.

12. The process as defined by claim 1, the reactive gas having a composition outside the explosive limits thereof.

13. The process as defined by claim 1, the reactive gas comprising an inert diluent therefor.

14. The process as defined by claim 1, said solid catalyst comprising said catalytically active phase deposited onto an inert support substrate therefor.

15. The process as defined by claim 14, said solid catalyst being in particulate state.

16. A process for the ammoxidation of a saturated hydrocarbon into an α,β-ethylenically unsaturated nitrile comprising reacting an acyclic alkane containing at least 3 carbon atoms per molecule with ammonia and oxygen, in vapor phase, to obtain an α,β-ethlenically unsaturated nitrile in the presence of a catalyst having a single catalytic active phase represented by the empirical formula (I):

$$Mo_a V_b M_c O_x \qquad (I)$$

wherein M is one or more elements selected from manganese, zinc, cobalt, copper, lithium, sodium, potassium or silver; a is a number ranging from 0.1 to 1; b is a number greater than zero and less than 2; c is a number greater than zero and less than 1; and x is determined by the oxidation number of the other elements thereof and said active phase represented by formula (I) being the sole ammoxidation catalytic component in the process.

* * * * *